(12) United States Patent
Trinkle et al.

(10) Patent No.: US 8,823,943 B2
(45) Date of Patent: Sep. 2, 2014

(54) SYSTEM AND METHOD FOR SEPARATING SAMPLES IN A CONTINUOUS FLOW

(75) Inventors: Linda Trinkle, Albuquerque, NM (US); Thomas Duensing, Albuquerque, NM (US)

(73) Assignee: Intellicyt Corporation, Albuquerque (MX)

( * ) Notice: Subject to any disclaimer, the term of this patent is extended or adjusted under 35 U.S.C. 154(b) by 263 days.

(21) Appl. No.: 13/321,809

(22) PCT Filed: May 21, 2010

(86) PCT No.: PCT/US2010/035740
§ 371 (c)(1),
(2), (4) Date: Nov. 21, 2011

(87) PCT Pub. No.: WO2010/135627
PCT Pub. Date: Nov. 25, 2010

(65) Prior Publication Data
US 2012/0061584 A1    Mar. 15, 2012

Related U.S. Application Data

(60) Provisional application No. 61/180,378, filed on May 21, 2009.

(51) Int. Cl.
*G01N 35/08* (2006.01)
*G01N 35/00* (2006.01)

(52) U.S. Cl.
CPC .................................... *G01N 35/00* (2013.01)
USPC ....................................................... 356/442

(58) Field of Classification Search
None
See application file for complete search history.

(56) References Cited

U.S. PATENT DOCUMENTS 3,698,870 A    10/1972  De Jong
3,921,439 A    11/1975  Burns
(Continued)

FOREIGN PATENT DOCUMENTS

EP    0 586 183    10/1999
EP    0 627 080    4/2000
(Continued)

OTHER PUBLICATIONS

Durack, Gary et al., "Time Interval Gating for Analysis of Cell Function Using Flow Cytometry", Cytometry vol. 12, Jul. 1991, 701-706.

(Continued)

*Primary Examiner* — Robert R Raevis
(74) *Attorney, Agent, or Firm* — Peacock Myers, P.C.; Janeen Vilven (57) ABSTRACT

One embodiment of the present invention provides for a method for identifying within a single record the location of each of a plurality of samples suspected of containing particles of interest wherein the single record is obtained from a flowing stream of the plurality of samples passing through a particle analyzer. The method comprises introducing into a conduit the plurality of samples suspected of containing particles of interest wherein each ones of the plurality of samples are separated by fluid gaps to produce a plurality of samples separated by fluid gaps and wherein each of the plurality of samples further comprises marker particles. The plurality of samples separated by fluid gaps are flowed through the conduit as a flowing sample stream to a detector of a particle analyzer, which may be a flow cytometer. The particles of interest are detected as the samples pass the detector of the particle analyzer.

12 Claims, 8 Drawing Sheets

(56) References Cited

U.S. PATENT DOCUMENTS

| | | |
|---|---|---|
| 4,053,282 A | 10/1977 | Hach et al. |
| 4,116,631 A | 9/1978 | Trinel et al. |
| 4,177,677 A | 12/1979 | Ruzicka et al. |
| 4,224,033 A | 9/1980 | Hansen et al. |
| 4,399,225 A | 8/1983 | Hansen et al. |
| 4,661,913 A | 4/1987 | Wu et al. |
| 4,714,682 A | 12/1987 | Schwartz |
| 4,767,206 A | 8/1988 | Schwartz |
| 4,774,189 A | 9/1988 | Schwartz |
| 4,853,336 A | 8/1989 | Saros et al. |
| 4,957,009 A | 9/1990 | Nohl et al. |
| 5,080,866 A | 1/1992 | Petty et al. |
| 5,084,394 A | 1/1992 | Vogt et al. |
| 5,221,521 A | 6/1993 | Hashizume |
| 5,268,147 A | 12/1993 | Zabetakis et al. |
| 5,286,452 A | 2/1994 | Hansen |
| 5,369,037 A | 11/1994 | Hansen |
| 5,374,398 A | 12/1994 | Isami et al. |
| 5,395,588 A | 3/1995 | North, Jr. et al. |
| 5,464,752 A | 11/1995 | Kortright et al. |
| 5,488,469 A | 1/1996 | Yamamoto et al. |
| 5,504,010 A | 4/1996 | Mitani et al. |
| 5,532,154 A | 7/1996 | Brown |
| 5,565,353 A | 10/1996 | Klebe et al. |
| 5,641,457 A | 6/1997 | Vardanega et al. |
| 5,694,486 A | 12/1997 | Shigeeda |
| 5,739,036 A | 4/1998 | Parris |
| 5,776,781 A | 7/1998 | Vardanega et al. |
| 5,788,927 A | 8/1998 | Farrell et al. |
| 5,824,269 A | 10/1998 | Kosaka et al. |
| 5,834,314 A | 11/1998 | Gates et al. |
| 6,074,879 A | 6/2000 | Zelmanovic et al. |
| 6,132,685 A | 10/2000 | Kercso et al. |
| 6,150,180 A | 11/2000 | Parce et al. |
| 6,156,178 A | 12/2000 | Mansfield et al. |
| 6,159,739 A | 12/2000 | Weigl et al. |
| 6,350,619 B1 | 2/2002 | Mercolino et al. |
| 6,727,071 B1 | 4/2004 | Dunlay et al. |
| 6,878,556 B2 | 4/2005 | Sklar et al. |
| 6,890,487 B1 | 5/2005 | Sklar et al. |
| 7,368,084 B2 | 5/2008 | Sklar et al. |
| 7,758,811 B2 | 7/2010 | Durack et al. |
| 7,842,244 B2 | 11/2010 | Sklar et al. |
| 8,021,872 B2 | 9/2011 | Sklar et al. |
| 8,268,571 B2 | 9/2012 | Sklar et al. |
| 8,637,261 B2 | 1/2014 | Sklar et al. |
| 2004/0214314 A1 | 10/2004 | Srienc et al. |
| 2005/0112541 A1 | 5/2005 | Durack et al. |
| 2006/0008924 A1* | 1/2006 | Anker et al. .................. 436/526 |
| 2006/0105371 A1* | 5/2006 | Fang et al. .................. 435/6 |
| 2007/0202608 A1 | 8/2007 | Uffenheimer et al. |
| 2010/0197512 A1 | 8/2010 | Trinkle et al. |
| 2011/0312536 A1 | 12/2011 | Sklar et al. |

FOREIGN PATENT DOCUMENTS

| | | |
|---|---|---|
| GB | 2 172 104 | 9/1986 |
| WO | WO-2010/005617 | 1/2010 |
| WO | 2010/135627 | 11/2010 |

OTHER PUBLICATIONS

Herzenberg, Leonore et al., "Interpreting Flow Cytometry Data: A Guide for the Perplexed", Nature Immunology vol. 7, No. 7, Jul. 2006, 681-685.

Lindberg, Walter et al., "Flow Injection Cytometry: A New Approach for Sample and Solution Handling in Flow Cytometry", Cytometry vol. 14 No. 2, 1993, 230-236.

Nolan, John P. et al., "A Rapid Mix Flow Cytometer with Subsecond Kinetic Resolution", Cytometry vol. 21 No. 3, May 1995, 223-229.

Pennings, Arie et al., "Improved Flow Cytometry of Cellular DNA and RNA by On-Line Reagent Addition", Cytometry vol. 8 No. 3, 1987, 335-338.

Robinson, J. P. et al., "An Innovation in Flow Cytometry Data Collection and Analysis Producing a Correlated Multiple Sample Analysis in a Single File", Cytometry vol. 12, No. 1, 1991, 82-90.

* cited by examiner

SYSTEM AND METHOD FOR SEPARATING SAMPLES IN A CONTINUOUS FLOW

CROSS-REFERENCE TO RELATED APPLICATIONS

This application claims priority to and the benefit of the filing of U.S. Provisional Patent Application Ser. No. 61/180,378 entitled "System and Method for Separating Samples in a Continuous Flow", filed on May 21, 2009, and the specification and claims thereof are incorporated herein by reference.

STATEMENT REGARDING FEDERALLY SPONSORED RESEARCH OR DEVELOPMENT

NA

INCORPORATION BY REFERENCE OF MATERIAL SUBMITTED ON A COMPACT DISC

NA

COPYRIGHTED MATERIAL

NA

BACKGROUND OF THE INVENTION

1. Field of the Invention (Technical Field)

Embodiments of the present invention relates to a system and method for sample handling and analysis of a continuous flow of samples by a particle analyzer.

2. Description of Related Art

Note that the following discussion refers to a number of publications by author(s) and year of publication, and that due to recent publication dates certain publications are not to be considered as prior art vis-a-vis embodiments of the present invention. Discussion of such publications herein is given for more complete background and is not to be construed as an admission that such publications are prior art for patentability determination purposes.

Flow cytometers are used to analyze biological cells and particles in a fluid sample by intersecting a thin stream of the fluid sample by an illumination source, usually a laser beam. The resulting light scatter (forward and right angle (side) scattered light) and fluorescent light is analyzed with one or more photomultiplier tubes (PMTS). The fluorescence channels of a flow cytometer are each set with barrier filters to detect a selected specific dye having a desired wavelength while filtering out signals from other wavelengths.

U.S. Pat. Nos. 4,714,682, 4,767,206, and 4,774,189, and U.K. Pat. No. 2,172,104 describe calibration of a flow cytometer using highly uniform microbeads which have excitation and emission spectra that match that of the unknown samples, as well as describing the synthesis and composition of said highly uniform microbeads. Matching spectra of microbeads and cells in this way allows direct comparison of data among flow cytometers which have different barrier filters so long as the sample and the calibration microbeads are analyzed under comparable instrument conditions and settings. Each sample that flows past the illumination source and is detected by the photomultiplier tube is recorded as a separate data file for analysis.

U.S. Pat. No. 5,084,394 describes the combined use of calibrated fluorescent biological cells with calibrated fluorescent microbeads to compensate for different responses of different flow cytometers. U.S. Pat. Nos. 6,074,879 and 6,350,619 describes novel methods for calibrating or standardizing flow cytometry instruments using synthetic polymer particles or beads having physical properties which provide advantages for their use in such instruments.

All of these methods require that a separate data file is obtained for each separate sample analyzed and therefore there is no difficulty in identifying the beginning and end for each sample even though the number of particle events within the sample are low. The totality of these patents and all other patents and any other publications cited herein and/or referred to in the Cross-Reference to Related Applications is hereby incorporated herein by reference.

BRIEF SUMMARY OF THE INVENTION

One embodiment of the present invention provides for a method for identifying within a single record the location of each of a plurality of samples suspected of containing particles of interest wherein the single record is obtained from a flowing stream of the plurality of samples passing through a particle analyzer. The method comprises introducing into a conduit the plurality of samples suspected of containing particles of interest wherein each ones of the plurality of samples are separated by fluid gaps to produce a plurality of samples separated by fluid gaps and wherein each of the plurality of samples further comprises marker particles. The plurality of samples separated by fluid gaps are flowed through the conduit as a flowing sample stream to a detector of a particle analyzer. The particle analyzer is for example a flow cytometer. The particles of interest when present and/or marker particles are detected as the plurality of samples pass the detector of the particle analyzer. A record over time for the particles of interest when present and/or marker particles in each of the plurality of samples are obtained in the single file once the plurality of samples pass the incident beam of light of the particle analyzer. A time position in the record is identified where particles of interest within any one of the plurality of samples would be located if present based upon the detection of marker particles present within each combined sample from the flowing stream of the plurality of samples.

Another embodiment provides a method for identifying within a single record the location of each of a plurality of samples suspected of containing particles of interest wherein the single record is obtained from a flowing stream of the plurality of samples passing through a particle analyzer. The method comprises introducing into a conduit the plurality of samples suspected of containing particles of interest wherein each ones of the plurality of samples are separated by fluid gaps to produce a plurality of samples separated by fluid gaps. Marker particles are introduced into a conduit between the ones of the plurality of samples separated by fluid gaps. The plurality of samples separated by fluid gaps and further separated by aliquots of marker particle are flowed through the conduit as a flowing sample stream to a detector of a particle analyzer. The particle analyzer is for example a flow cytometer. Particles of interest when present and/or marker particles are detected as the plurality of samples and the marker particle aliquots pass the detector of the particle analyzer. A record over time for the detected particles of interest when present and/or marker particles are obtained once the flowing stream passes the incident beam of light of the particle analyzer. A time position in the record is identified where particles of interest within any one of the plurality of samples would be located if present based upon the location of the marker particles within the record.

In a preferred embodiment, introducing into a conduit the plurality of samples includes uptaking each of the plurality of samples from the respective sample container. For example, the respective sample container is a microplate having rows and columns of sample wells for holding samples to be tested.

In another embodiment, a sampling order of the rows and columns of the sample wells is determined by the user. For example, the sampling order is correlated with the identifying a time position in the record where particles of interest within any one of the plurality of samples would be located if present to identify the location on the sample well from which the sample was uptaken.

According to one embodiment, fluid gaps are gas gaps, for example air gaps.

According to another embodiment, flowing the plurality of samples includes moving the samples with a pump, gravity, acoustic means, microcapillary action, pressurization or any combination thereof.

According to another embodiment, detecting particles of interest when present depends on the optical and/or physical characteristic of interest selected for the particles of interest. According to another embodiment detecting marker particles depends on the optical and/or physical characteristics selected for the marker particles. For example, marker particles are selected based upon optical and/or physical characteristics which may be the same or different from the optical and/or physical characteristics of the particles of interest.

One aspect of one embodiment of the present invention provides a method for identifying individual samples in a continuous flowing stream. Another aspect of one embodiment of the present invention provides a method for analyzing samples in a continuously flowing stream. Another aspect of one embodiment of the present invention provides for separating ones of a plurality of samples in a continuous flowing stream using a combination of air gaps and marker particles.

Another aspect of one embodiment of the present invention provides for positive identification of sample containers that do not have a measureable quantity of cells or beads in the sample preparation contained by the sample containers. Another aspect of one embodiment of the present invention provides for positive identification of wells which were not properly sampled due to instrument malfunction which may result in large variations in the shape of the sample curves when plotted over time.

Another aspect of one embodiment of the present invention provides for comparing the relative fluorescence of fluorescent marker beads to the treated cells as a consistency parameter for samples obtained from wells within a plate or plates for a flowing stream of samples in an experiment recorded in a single data file. Thus data obtained from multiple plates can be normalized to the beads, allowing direct comparison of results over large experimental data sets.

Further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Note that in the specification and claims, "about" or "approximately" means within twenty percent (20%) of the numerical amount cited.

As used herein "a" means one or more.

As used herein "well" means structure which holds/contains a sample to be analyzed, control or aliquot of marker particles.

As used herein "microplate" and "plate" refer to a structure capable of holding one or more samples to be analyzed or aliquot of marker particles.

As used herein "sample" refers to any quantity of liquid which may contain particles of interest or marker particles that are detectable by a particle analyzer.

As used herein "marker particles", "control particles", "beads" and "microbeads" are used interchangeable and refer to one or more particles that is detectable by a particle analyzer. A population of marker particles shares at least one physical and/or optical property among the members of the marker particle population.

Figure 9:
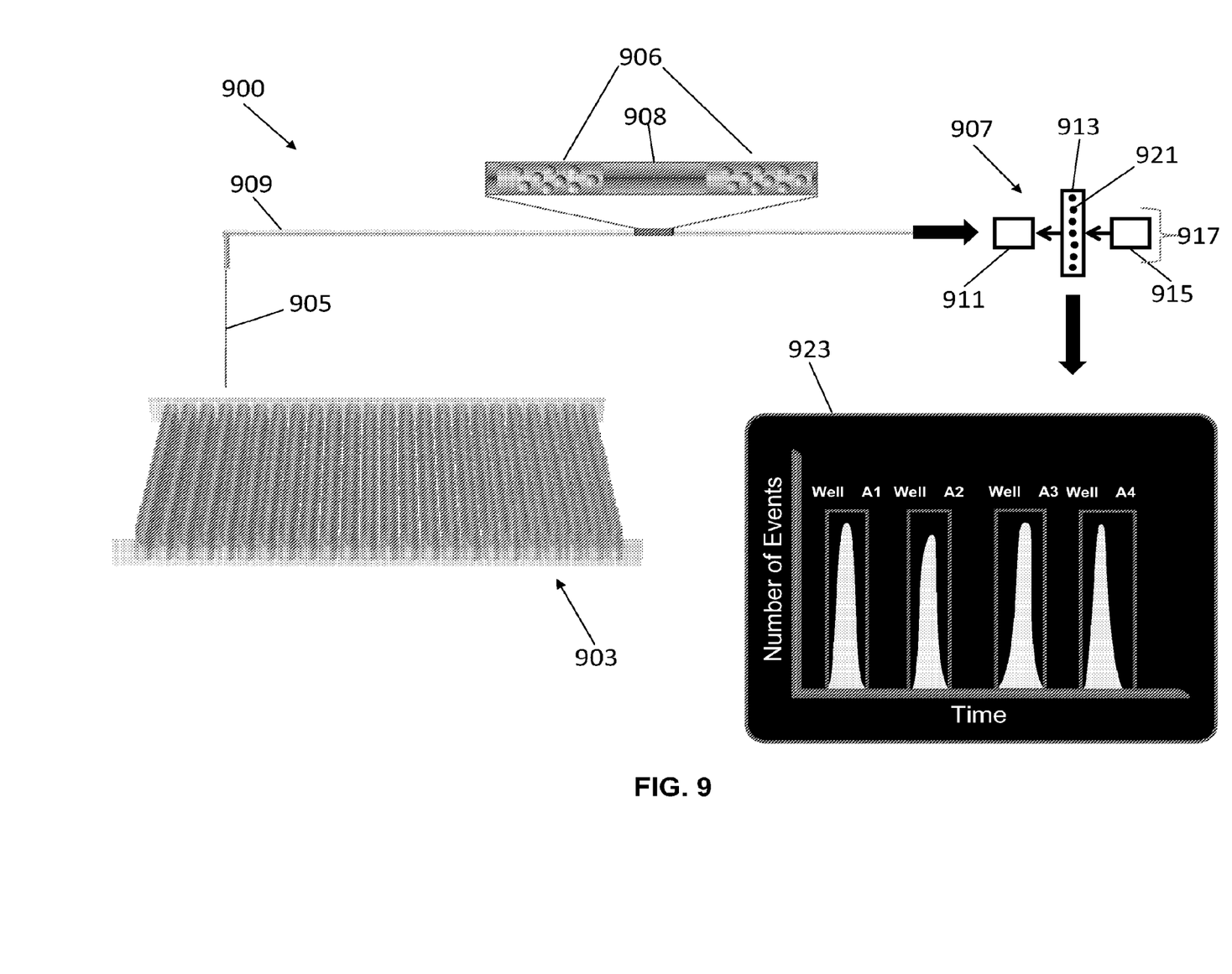
FIG. 9 illustrates a particle analyzer system useful in the method as described herein.

A particle analyzer system (for example a system as described in U.S. Pat. No. 6,878,556 and WO2010005617) uptakes from a sample container an aliquot of a sample suspected of having within the sample particles for analysis (sample to be analyzed). An illustrative system 900 as described herein is shown in FIG. 9. The system comprises a sample to be analyzed 906 which is transported from a sample container 903 to a detector 911 of the particle analyzer 907 via a conduit 909. The sample to be analyzed 906 is taken up from the sample container 903 via a probe 905. In between samples, the probe uptakes a separation gas 908. Multiple samples can be transported in the conduit sequentially. The multiple samples are separated from each other via fluid gaps (e.g. air) 908 and a plurality of samples to be analyzed are moved along the conduit to the detector 911 thereby creating a flowing stream of samples to be analyzed. Particles 921 within the sample to be analyzed 906 flow in the flow cell 913 and pass an illumination source 915 in the detector zone 917. The demarcation/delineation between the plurality of samples to be analyzed in the flowing stream within the conduit is the fluid gap positioned between each one of the plurality of samples to be analyzed. For example, a first sample to be analyzed is separated from a second sample to be analyzed via one or more air gaps according to one embodiment of the present invention.

Figure 6:
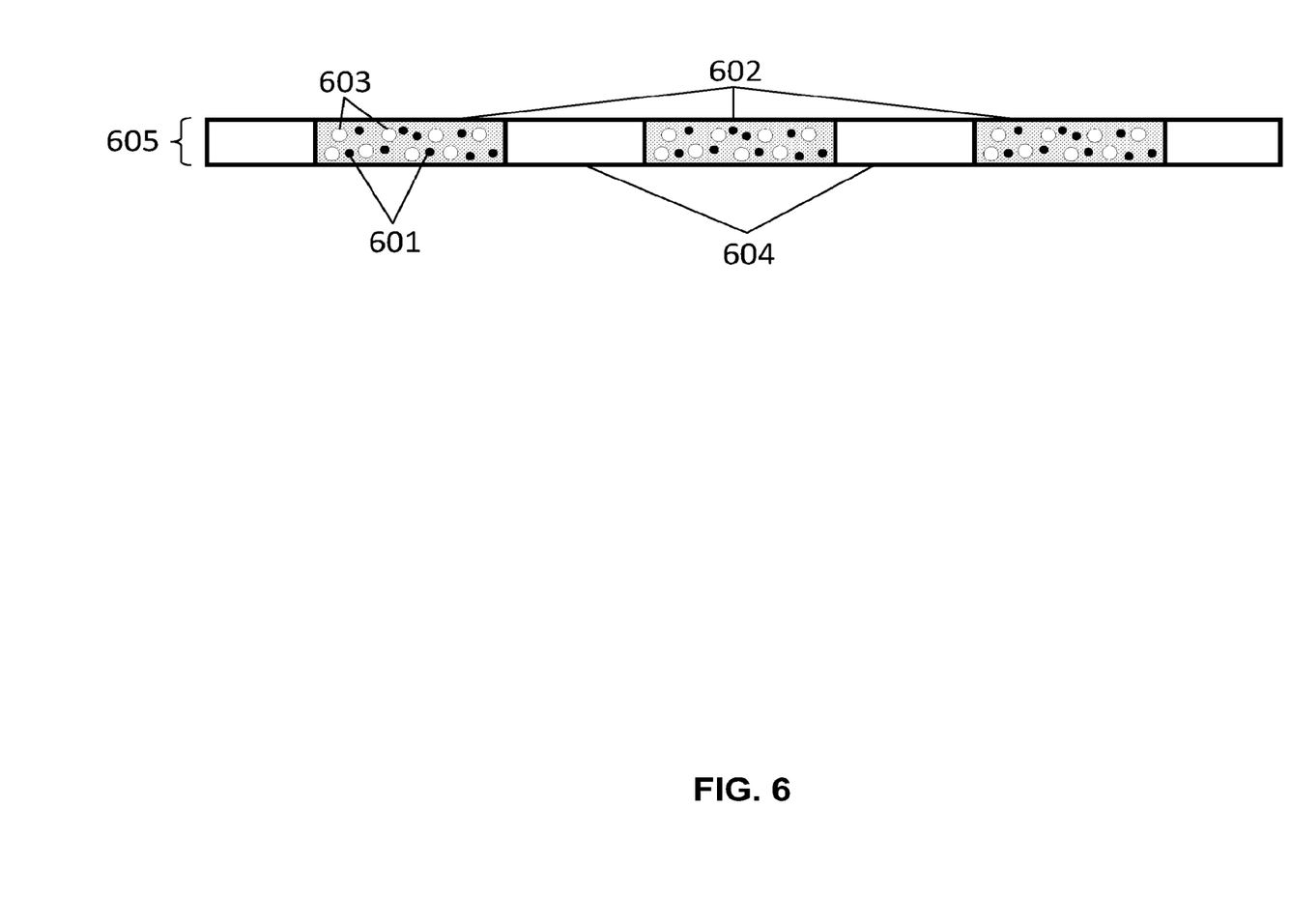
FIG. 6 illustrates a plurality of samples in a conduit according to one embodiment of the present invention.

In another embodiment, the system and method utilizes marker particles 601 to identify the location within the sample stream of a sample to be analyzed 602 when the marker particles are comingled with the sample to be analyzed as is illustrated in FIG. 6. When marker particles are not present, the delineation of each sample to be analyzed in the sample stream is easily identified when particles of interest 603 in the samples to be analyzed 602 are relatively similar in terms of their concentration and/or other optical and/or physical characteristics. If the multiple samples to be analyzed in the conduit 605 are different with respect to the particles of interest—for example, if there a very few particles of interest in some of the samples to be analyzed, or if there are large gaps inserted between the air gaps 604 where a sample to be analyzed would be expected but for an instrument malfunction—the location of the sample to be analyzed in the data stream becomes problematic in the absence of marker particles.

One embodiment of the present invention provides that marker particles are comingled with a sample to be analyzed. The flow cytometric properties of the marker particles may be different from those of the particles of interest within the samples to be analyzed. The difference in the optical and/or physical characteristics of the marker particles along with the fact that there may be known numbers of marker particles comingled with each sample to be analyzed allows a user to delineate the location of the sample to be analyzed in the data stream even if there are no particles of interest in the sample to be tested other than the marker particles.

Figure 3:
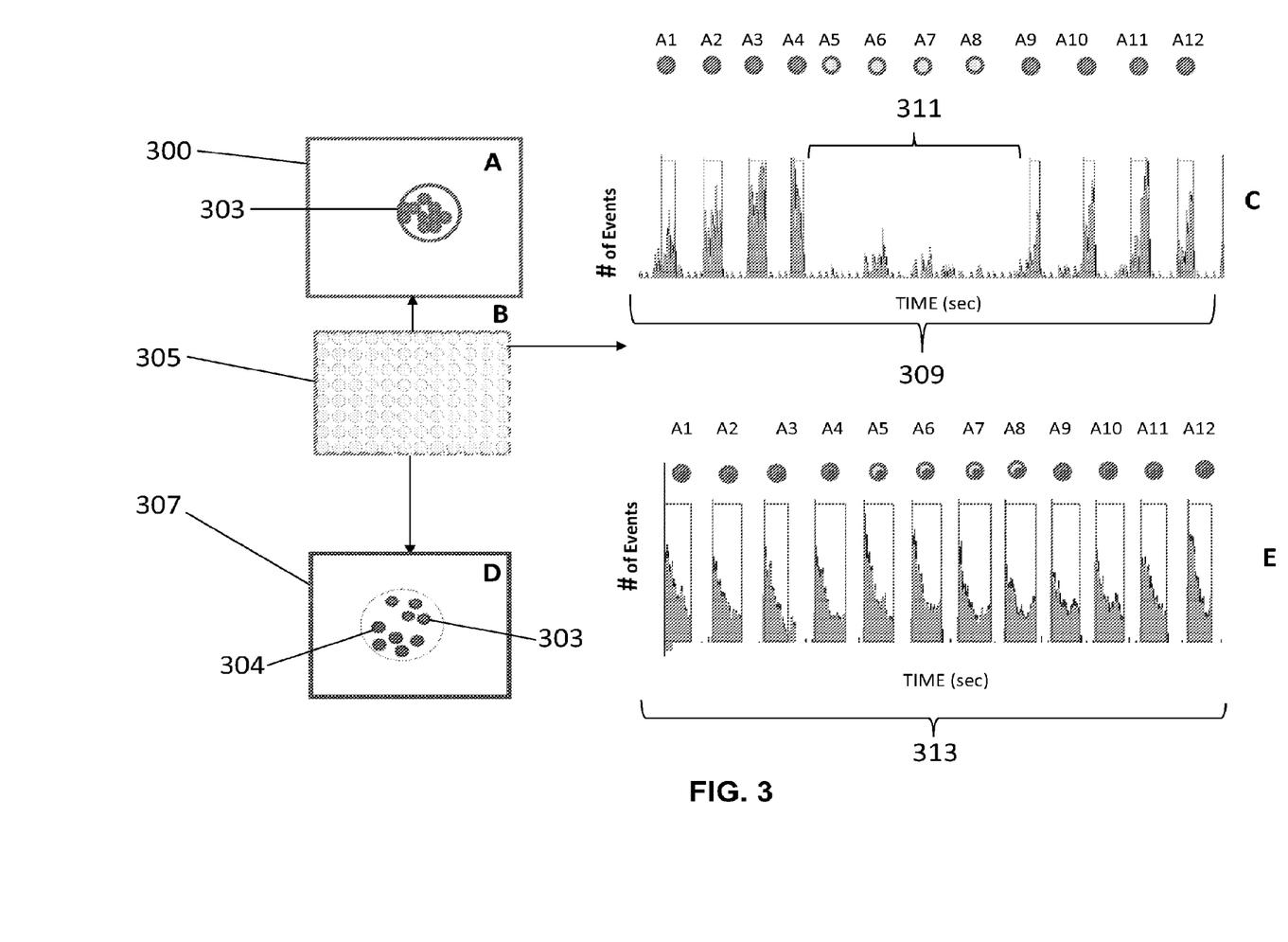
FIG. 3 illustrates data obtained from a plurality of samples detected with a particle analyzer in a single file with and without control particles added to each sample according to one embodiment of the present invention.

Referring now to FIG. 3, a system and method for distinguishing between sample wells during sample uptake is illustrated. Sample plate 300 of FIG. 3A may contain a well having one or more particles in a sample well 303. Typically a sample plate 305 will have multiple wells containing sample to be analyzed as is illustrated in FIG. 3B showing wells A1, A2, A3, A4, A5, A6, A7, A8, A9, A10, A11, and A12. A well may contain both marker particles 304 (red) and particles of interest 303 (blue) within a sample. A plurality of samples to be analyzed which may or may not contain particles are introduced into a particle analyzer as a flowing stream of sequential samples to be analyzed. Each sample to be analyzed is separated by a gas (fluid) gap which is introduced in the flowing stream of samples as each sample to be analyzed is withdrawn from a plurality of wells from a sample plate. Each one of the plurality of samples to be analyzed in the flowing stream is analyzed as it passes a light interrogation source and a detector (detector zone). Information about the scattered and emitted light as each particle passes through the light path, is collected by a processor and saved in a single data file. The number of events (particles detected) for each sample over time are recorded (data stream) as is illustrated in FIG. 3C. A1, A2, A3, A4, A5, A6, A7, A8, A9, A10, A11, A12 are samples from 1 row of plate 305 analyzed by a flow cytometer connected to a continuous flow sampling device such as a HyperCyt® (IntelliCyt Corporation, Albuquerque, N. Mex.). There is an air gap between samples. Data are recorded and displayed over time as illustrated in 309. As is illustrated in 311 for samples A5, A6, A7 and A8 when there are few events (particles of interest detected) within a sample to be analyzed, the number of events are low and not consistent. A low number of events in a sample makes it difficult to identify the boundaries for each of the samples of interest A5, A6, A7 and A8 for time zone 311 in the data stream.

Referring now to FIG. 3D, sample wells may contain a sample to be analyzed having particles of interest 303 (blue circles) and marker particles 304 (red circles) comingled therein. The marker particles 304 may have optical and/or physical characteristics that are different from the particles of interest 303 in the sample to be analyzed, thereby allowing detection of the marker particles 304 in addition to detection of the particles of interest 303 in the sample to be analyzed. FIG. 3E illustrates an event profile (histogram) over time 313 for the particles of interest in the sample to be analyzed and the marker particles for each sample taken from wells A1, A2, A3, A4, A5, A6, A7, A8, A9, A10, A11 and A12. The marker particles may be comingled with the sample to be analyzed in a sample well or can occupy a separate well having no sample to be analyzed. For FIG. 3E, samples from wells A5, A6, A7, A8 are clearly delineated by the marker particle profile thereby marking the boundaries in the data stream for the location where a sample to be analyzed would be if a sample to be analyzed were taken up by the system. For FIG. 3E, the red circles indicate marker particles and the blue circles indicate particles of interest detected.

Marker particles can be added to a well containing sample or a non-sample containing well. The marker particles may have a known characteristic such as known size, fluorescent intensity, forward light scatter and side light scatter for example. However, other characteristics that are well known in the art for detecting and characterizing particles are useful in a particle analyzer such as the particle analyzer disclosed in U.S. Pat. No. 6,878,556 is also useful.

Figure 4:
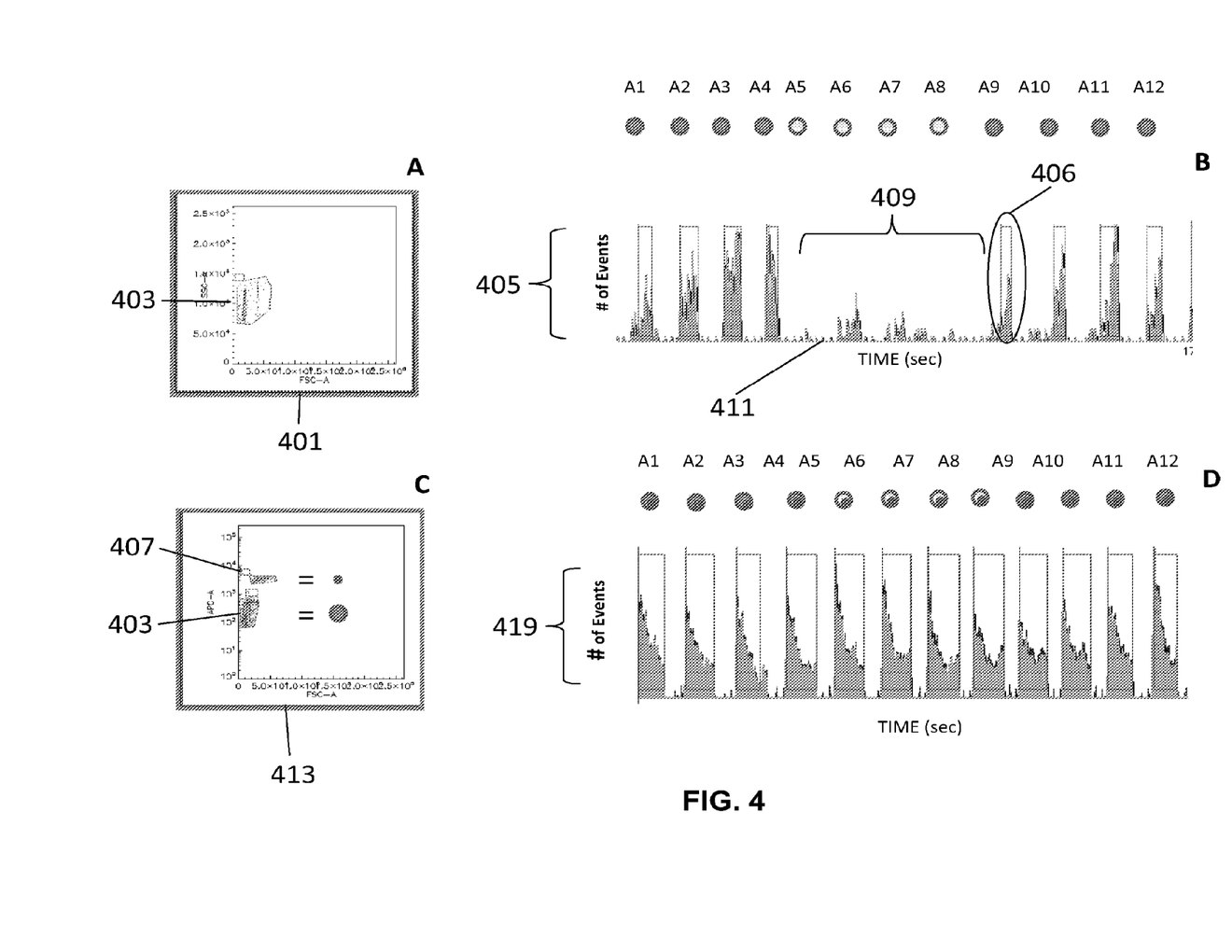
FIG. 4 illustrates particle analyzer data using one embodiment of the present invention for sample identification in a flowing stream of samples in which particles with a different fluorescence characteristic were detected with a particle analyzer.

Referring now to FIG. 4A, dot plot 401 illustrates forward light scatter versus side angle light scatter for particles of interest in a sample to be analyzed. Particles having the light scatter profile 403 are recorded as events over time for each sample to be analyzed that passes through the interrogation light source to produce graph 405 in FIG. 4B. Since some samples to be analyzed have few particles, the number of events over time that are recorded are low as is depicted for time period 409. Because there are significant differences in the numbers of particles per sample to be analyzed that passes the detector at time period 409 as compared to samples before and after this period. The overall low numbers of particles per sample results in an inability to set time bin gates such as 406 that were required to differentiate events between each sample during the period identified in 409.

Referring now to 413 of FIG. 4C, a dot plot is illustrated for marker particles 407 comingled with particles of interest 403 in a sample to be analyzed. Since marker particles are added to each sample to be analyzed, the location of an individual sample to be analyzed in a data stream 419 of FIG. 4D is determinable from the gates set in the dot plot of FIG. 4C at 403 and 407. Graph 419 illustrates the number of events recorded over time from each sample to be analyzed in the flowing stream comprising the plurality of samples separated by air gaps as each of the plurality of samples passes an interrogation source. For example, samples are introduced from each well by continuous flow into the particle analyzer. A histogram recorded over time for each of the samples to be analyzed is obtained from a plurality of wells and represents a data stream. The number of events on the y axis of graph 419 are more consistent with the addition of the marker particles than without (graph 405). Each population of particles 403 and 407 can be determined from the time bins in the graph of FIG. 4D. Data from the particles of interest (for example 403) can then be analyzed based upon the automatic gating made possible by the clear delineation of each sample population.

In another embodiment of the present invention, the marker particles are introduced between samples, and thus demarcate the anticipated beginning location in the flowing stream of a sample to be analyzed prior to the sample to be analyzed entering the detector zone of the particle analyzer. Once the bolus of sample to be analyzed moves past the detector zone, a subsequent bolus of marker particles in the conduit moves past the detector zone indicating the anticipated ending location in the flowing stream of a sample to be analyzed. These marker particles have known physical and/or optical characteristics, including emission spectra, intensity, shape, size, which are captured by the particle analyzer (e.g. flow cytometer). The marker particles are added in known positions relative to the samples to be analyzed in the flowing stream. The data analysis method then utilizes the characteristics and the temporal position within the flowing stream of the marker particles to determine the anticipated location of a sample to be analyzed in the flowing stream and/or data stream.

Figure 7:
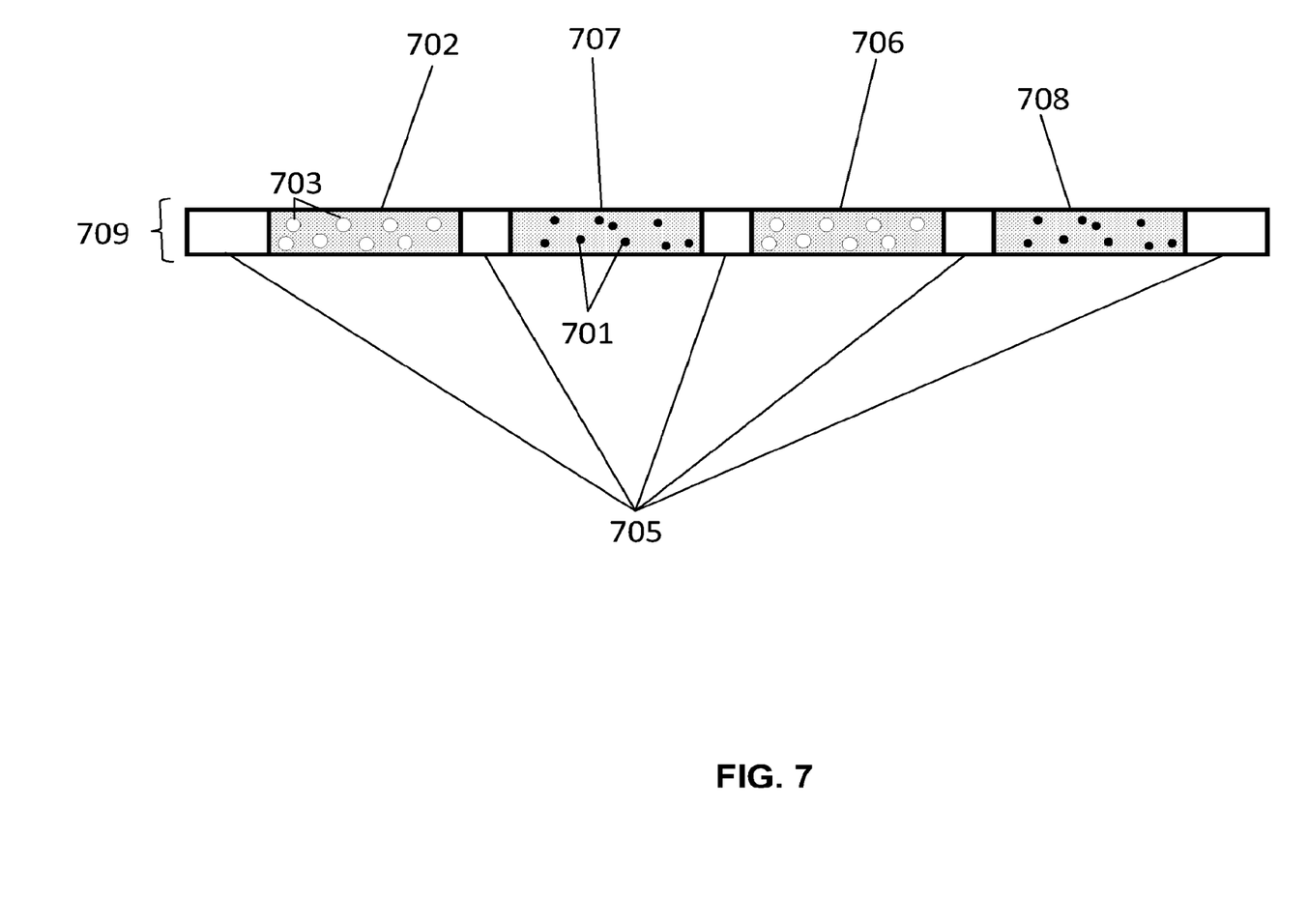
FIG. 7 illustrates a plurality of samples in a conduit according to one embodiment of the present invention.

Referring now to FIG. 7, for example, an aliquot 707 of marker particles 701 is introduced between a first sample 706 and second sample 702 or at other intervals between each sample. Further, samples to be analyzed are taken up (e.g. aspirated) from sample containers (e.g. wells of a plate) via a probe or autosampler. Each aliquot 707 and 708 of marker particles 701 may be separated one from the other in the flowing stream by separation fluid such as gaps of air 705 (but not limited thereto as other gases as an example of fluids are also suitable as a separation fluid). The flowing stream of samples to be analyzed is delivered to the particle analyzer and data from the plurality of samples and marker particles in the flowing stream may be acquired by a processor and/or stored in a single data file.

An autosampler probe of a particle analyzer uptakes an aliquot of a marker particle solution from a marker particle container (e.g. wells or troughs of a plate, or dispensing reservoir) followed by a sample to be analyzed from a sample well. This results in aliquots 707 and 708 of marker particles 701 positioned in a conduit 709 in between each sample to be analyzed. This alternating sampling process is repeated until all the samples to be analyzed from the plurality of sample containers (e.g. wells) have been sampled by the probe. The marker particles 701 in each aliquot 707 and 708 are detected and the particles in each aliquot are identified as events recorded in a single file over time as the stream of marker particle aliquots flows past the detector.

Figure 8:
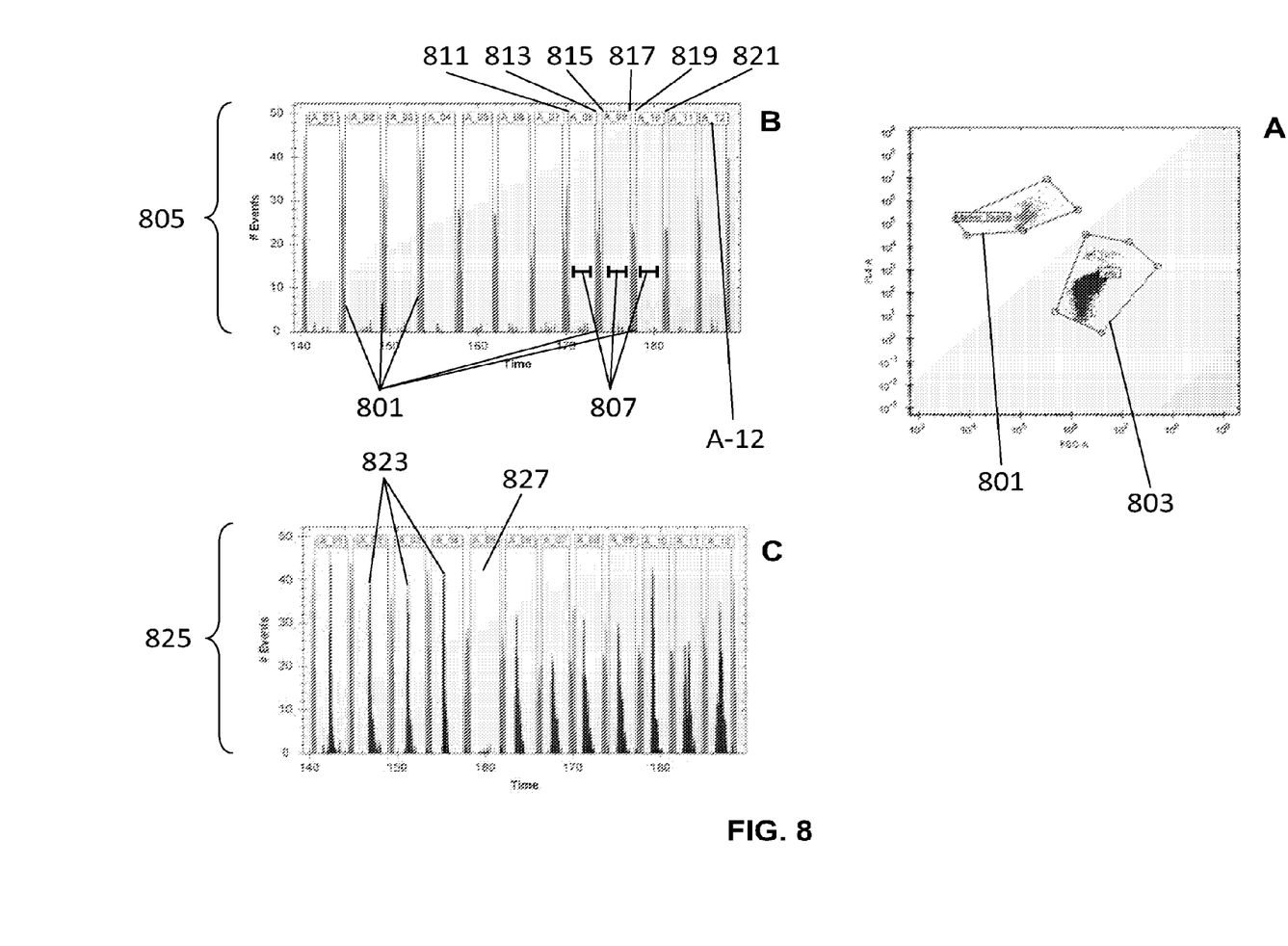
FIG. 8 illustrates particle analyzer data for one embodiment of the present invention for sample identification in a flowing stream of samples.

Referring now to FIG. 8, boundaries (811 and 813); (815 and 817); , (819 and 821) represent time gates which are easily positioned before and after a marker particle histogram 801 to designate the time gates of the location for a samples to be analyzed 807 when present. Sample A08 will reside in between the pair of time gates boundaries 811 and 813 for example.

The time boundaries 807, of each sample to be analyzed when present, is set based on the lowest number of events associated with each marker particle histogram for example 811 and 813. The correlation of a histogram back to the x-y coordinates of a sample container (for example A12 position of a well on a plate) is determined by the timing and sampling order used in the sampling process. Test sample data in 825 of FIG. 8C illustrates a graph of the marker particle data in 805 and particles of interest 803 in the samples to be analyzed together. Since the samples to be analyzed and marker particles alternate in the conduit, each histogram peak of a sample to be analyzed 823 appears at a unique time period and can be assigned to the sample well identified by the marker particle data. The advantage of this method is that in experiments that are performed with an autosampler sampling system as described herein, there are often cases when individual wells of the plate contain no sample events 827 due to sampling error or effects of chemical treatment of the sample. Moreover, it is not known in advance which wells will be empty of test sample events. With this method, wells that contain no test sample events can be accurately identified via the marker particle histograms. FIG. 8A represents a dot plot showing a population of marker particles 801 and particles of interest 803.

One aspect of one embodiment of the present invention provides delineation between samples to be analyzed when the samples to be analyzed are acquired in a flowing stream separated by air gaps for example. There are often cases when an individual well of the plate contains no particles and therefore no events to detect by the particle analyzer due to sampling error or effects of chemical treatment of the sample. Moreover, it is not known in advance which wells will be empty of particles to be analyzed/events. With this method, wells that contain no test sample events can be accurately identified via the marker particle peaks.

From a sample to be analyzed, a population of particles is identified based upon their optical/physical characteristics such as light scatter, emission properties, size, but not limited thereto. Particles from the plurality of samples to be analyzed sharing the desired characteristic (particles of interest) are detected by the detector in the detector zone as the particles of interest pass between the detector and a light source that provides a light path that strikes the detector within the detector zone. As the samples to be analyzed pass the detector (e.g. photomultiplier tube) of the particle analyzer, samples having particles of interest with optical and/or physical characteristics that are within the desired/set optical and/or physical characteristics will be identified as an event (particle having or producing the desired optical and/or physical properties for analysis). The air gaps between the samples do not contain particles of interest that will be recorded as an event.

Data is detected for marker particles that match the desired light scatter characteristics (or another physical or optical feature of interest selected) and the data are acquired for each of the particles of interest in the plurality of samples and marker particles in a single file over time (data stream).

Since the events are recorded over time, a high resolution time parameter is also recorded during sample data acquisition (data stream). Event voids/gaps are created in the data stream by the passage of the air gaps, allowing the particles of interest from each sample to be analyzed to be distinguished one from the other and separately evaluated when plotted in conjunction with the time parameter. Based on this temporal distribution of events, data histogram peaks (representing events acquired) are identified and assigned to individual sample containers (wells of the microplate) based upon the sampling instructions and sequence of introduction of the plurality of samples to be analyzed into the conduit.

Marker particles having a second optical and/or physical characteristic that may be the same or different from the optical and/or physical characteristic of the particles of interest in the samples to be analyzed are taken up in the conduit at discrete intervals before and/or after the plurality of samples to be analyzed. For example the marker particles are introduced into the conduit after and/or before an air gap. According to one embodiment of the present invention, air gaps immediately precede or follow in the conduit the anticipated location of a sample to be analyzed. The marker particles delineate, within the flowing stream of samples, a location where a sample to be analyzed should be located.

Figure 1:
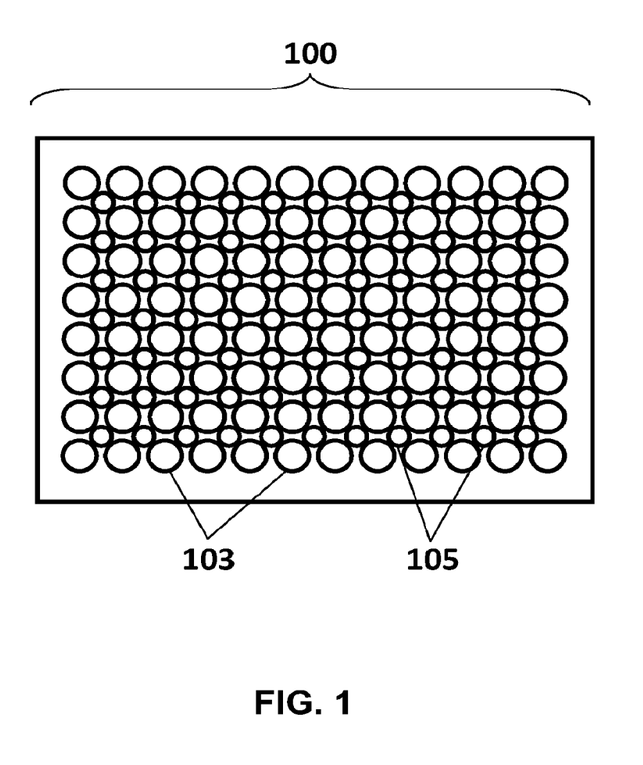
FIG. 1 illustrates one embodiment of the present invention with a plurality of wells of a sample plate having marker particles positioned in wells that are interspersed between sample wells.

Referring now to FIG. 1, another embodiment of the present invention provides a sample container 100 having a plurality of wells for holding samples to be analyzed but not limited thereto as the wells may also hold solutions of buffer and/or marker particles for example. The wells may also function as reaction vessels. The wells are arranged in a matrix having predetermined rows, columns, well volume, height, length, width, well diameter, well depth and well-to-well spacing. In one embodiment of the present invention, wells for holding samples to be analyzed 103 have different dimensions from the wells for holding marker particles 105 as is illustrated in FIG. 1. The wells for marker particles may be dispersed periodically between and/or among the wells for samples to be analyzed.

Figure 2:
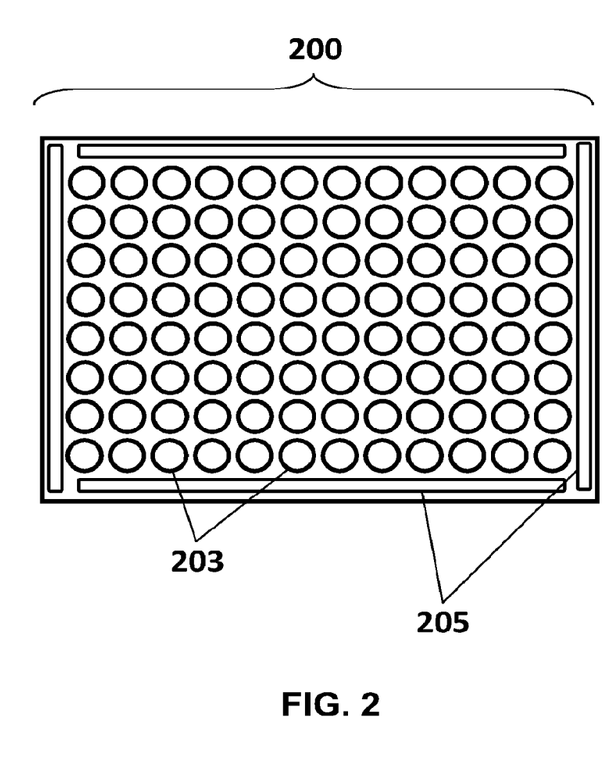
FIG. 2 illustrates another embodiment of one embodiment of the present invention with a plurality of wells on a sample plate having marker particle troughs positioned on the sample plate.

Referring now to FIG. 2, a sample container 200 may contain wells for the samples to be analyzed 203 and troughs 205 for the marker particles according to one embodiment of the present invention. The presence of the wells for marker particles, along with the known sampling order of these wells or troughs compared to the sampling order of the wells holding or intended to hold the samples to be analyzed, allows a user to accurately identify the wells from which the test samples are located or should be located.

Another embodiment of the present invention provides for the use of marker particles to match data for each sample to be analyzed with the sample container from which the sample to be analyzed was withdrawn. For example, unique combinations of marker particles are added to one or more of the plurality of sample wells as a unique bar code. The unique bar code may be comingled with samples to be analyzed. The physical and/or optical characteristics of the unique bar code allows identification of the sample to be analyzed and the location on a plate from where the sample to be analyzed was taken.

Figure 5:
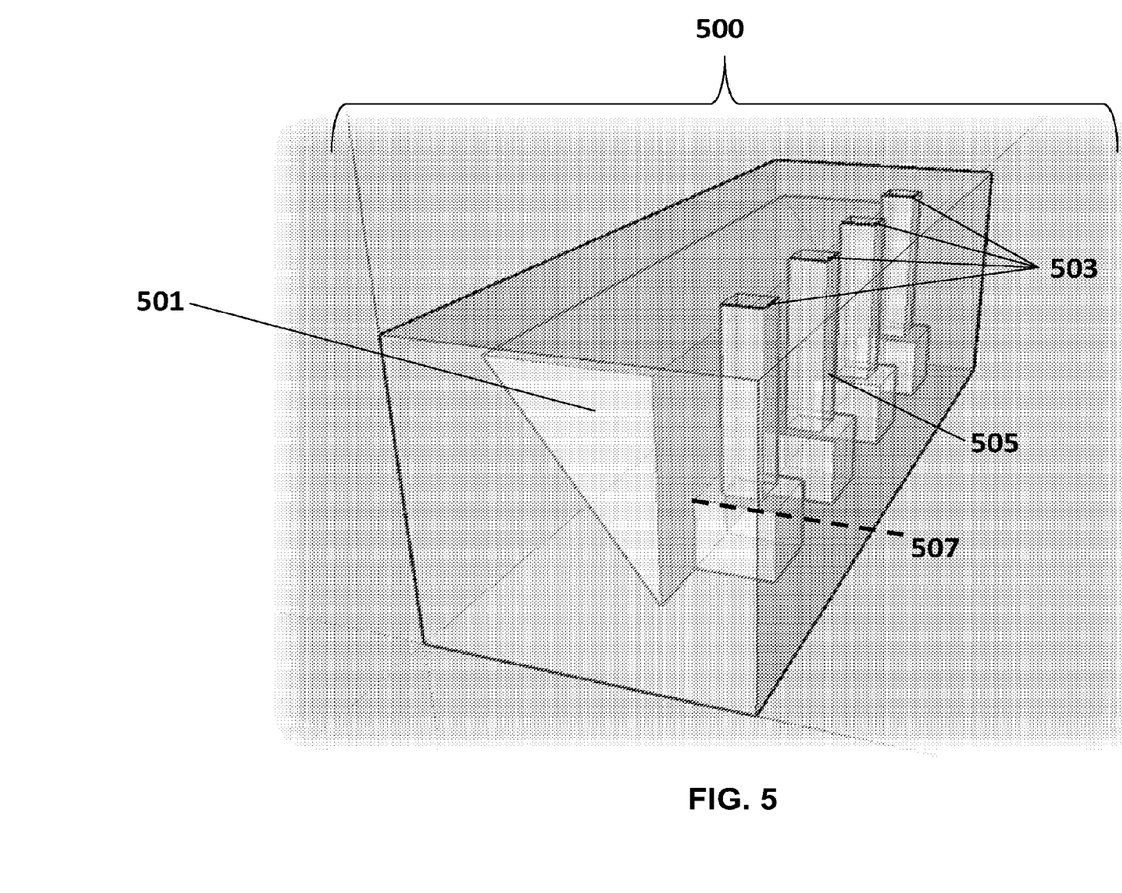
FIG. 5 illustrates a sample reservoir according to one embodiment of the present invention.

In another embodiment, the marker particles are located in a marker particle reservoir 500 of FIG. 5 that maintains a concentration of marker particles in the reservoir at a minimum volume and level 507 throughout a sampling cycle when aliquots of the marker particles are withdrawn multiple times from a sampling port 503.

According to one embodiment the dispensing reservoir 500 may be located apart from a microplate. The dispensing reservoir comprises a storage vessel 501 having a capacity for a given volume of a marker particle solution and a sampling vessel having a sampling port wherein the sampling vessel and a storage vessel 501 are in fluid communication at 507. The storage vessel 501 is positioned at a height relative to the sampling vessel 505 such that the volume of the marker particle solution in the storage vessel 501 supplies the sampling vessels 505 with a constant volume of the marker particle solution throughout the sampling process which volume is dependent on the atmospheric pressure and the height of the storage vessel 501 relative to the sampling vessel 505.

Further, the sampling vessel 505 may have a sampling port 503 that allows a probe to enter the sampling vessel 505 to a designated depth to withdraw the marker particle solution while minimizing marker particles coating the probe exterior surface. A reservoir 500 as described is illustrated in FIG. 5.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for identifying within a single record the location of each of a plurality of samples suspected of containing particles of interest wherein the single record is obtained from a flowing stream of the plurality of samples passing through a particle analyzer, the method comprising:
   introducing into a conduit the plurality of samples suspected of containing particles of interest wherein each ones of the plurality of samples are separated by fluid gaps to produce a plurality of samples separated by fluid gaps;
   introducing aliquots of marker particles into the conduit between the ones of the plurality of samples separated by fluid gaps wherein the aliquots of marker particles do not contain particles of interest and the marker particles have a different known optical and/or physical characteristic as compared to the s articles of interest within the plurality of samples;
   flowing the plurality of samples separated by fluid gaps and further separated by aliquots of marker particles through the conduit as a flowing sample stream to a detector of a particle analyzer;
   detecting particles of interest when present and/or marker particles as the plurality of samples and the marker particle aliquots pass the detector of the particle analyzer;
   obtaining in the single record a profile over time for the detected particles of interest when present and/or marker particles once the flowing stream passes an incident beam of light of the particle analyzer;
   identifying a time position in the single record where particles of interest within any one of the plurality of samples would be located if present based upon the location of the marker particles within the single record.

2. The method of claim 1, wherein introducing into a conduit the plurality of samples includes uptaking each of the plurality of samples from the respective sample container.

3. The method of claim 2, wherein the respective sample container is a microplate having rows and columns of sample wells for holding samples to be tested.

4. The method of clam 3, wherein a sampling order of the rows and columns of the sample wells are determined by the user.

5. The method of claim 4, wherein the sampling order is correlated with the identifying a time position in the record where particles of interest within any one of the plurality of samples would be located if present to identify the location on the sample well from which the sample was uptaken.

6. The method of claim 1, wherein flowing the plurality of samples includes moving the samples with a pump, gravity, acoustic means, microcapillary action, pressurization or any combination thereof.

7. The method of claim 1, wherein detecting particles of interest when present depends on the optical and/or physical characteristic of interest selected for the particles of interest.

8. The method of claim 1, wherein detecting marker particles depends on the optical and/or physical characteristics selected for the marker particles.

9. The method of claim 8, wherein the marker particles have a different optical and/or physical characteristics as compared to the particles of interest.

10. The method of claim 1, wherein the particle analyzer is a flow cytometer.

11. The method of claim 1, wherein fluid gaps are gas gaps

12. The method of claim 11, wherein the gas gaps are air gaps.

* * * * *